(12) United States Patent
Nock et al.

(10) Patent No.: US 8,371,443 B2
(45) Date of Patent: Feb. 12, 2013

(54) BIOPSY MARKER DELIVERY DEVICE

(75) Inventors: Andrew P. Nock, Centerville, OH (US);
Ramon Ramos, Loveland, OH (US);
Shailendra K. Parihar, Mason, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 395 days.

(21) Appl. No.: 12/564,315

(22) Filed: Sep. 22, 2009

(65) Prior Publication Data

US 2011/0071424 A1 Mar. 24, 2011

(51) Int. Cl.
*A61B 5/00* (2006.01)
(52) U.S. Cl. ........ 206/363; 600/407; 600/433; 606/116; 206/438
(58) Field of Classification Search .......... 600/562–572, 600/407, 414, 420, 424–435; 606/167, 170, 606/180, 116; 206/363, 438
See application file for complete search history.

(56) References Cited

U.S. PATENT DOCUMENTS

| | | | |
|---|---|---|---|
| 4,760,847 A * | 8/1988 | Vaillancourt | 606/185 |
| 5,526,822 A | 6/1996 | Burbank et al. | |
| 5,941,439 A * | 8/1999 | Kammerer et al. | 227/67 |
| 6,086,544 A | 7/2000 | Hibner et al. | |
| 6,200,274 B1 * | 3/2001 | McNeirney | 600/562 |
| 6,228,055 B1 | 5/2001 | Foerster et al. | |
| 6,371,904 B1 | 4/2002 | Sirimanne et al. | |
| 6,993,375 B2 | 1/2006 | Burbank et al. | |
| 6,996,433 B2 | 2/2006 | Burbank et al. | |
| 7,044,957 B2 | 5/2006 | Foerster et al. | |
| 7,047,063 B2 | 5/2006 | Burbank et al. | |
| 7,229,417 B2 | 6/2007 | Foerster et al. | |
| 2003/0109803 A1 | 6/2003 | Huitema et al. | |
| 2003/0233101 A1 * | 12/2003 | Lubock et al. | 606/116 |
| 2004/0124105 A1 * | 7/2004 | Seiler et al. | 206/363 |
| 2004/0236212 A1 * | 11/2004 | Jones et al. | 600/431 |
| 2004/0236213 A1 * | 11/2004 | Jones et al. | 600/431 |
| 2005/0119562 A1 * | 6/2005 | Jones et al. | 600/426 |
| 2005/0228311 A1 | 10/2005 | Beckman et al. | |
| 2007/0010738 A1 | 1/2007 | Mark et al. | |
| 2007/0118048 A1 | 5/2007 | Stephens et al. | |

* cited by examiner

*Primary Examiner* — Rene Towa
(74) *Attorney, Agent, or Firm* — Frost Brown Todd LLC

(57) ABSTRACT

A biopsy marker delivery device are described. The delivery device can include a relatively flexible hollow tube, a pushing member such as a push rod disposed for sliding with the tube, and at least one marker disposed in the tube. A marker blocking member is disposed distal of the distal most marker, and is disposed at least partially within the hollow tube to assist in preventing premature deployment of a marker from the hollow tube. A portion of the blocking member may disposed in the hollow tube, and another portion of the member may be operatively associated with a portion of the package such that when the marker delivery device is removed from the package, the member is removed from the marker delivery device.

20 Claims, 6 Drawing Sheets

BIOPSY MARKER DELIVERY DEVICE

CROSS REFERENCE TO RELATED APPLICATIONS

This application cross references and incorporates by reference commonly assigned U.S. patent application Ser. No. 12/196,301 filed Aug. 22, 2008. This application is related to biopsy marker delivery devices, including packaging of such devices and members for preventing premature deployment of markers.

BACKGROUND

Biopsy samples have been obtained in a variety of ways in various medical procedures using a variety of devices. An exemplary biopsy device is the MAMMOTOME® brand device from Ethicon Endo-Surgery, Inc. of Cincinnati, Ohio. Biopsy devices may be used under stereotactic guidance, ultrasound guidance, MRI guidance, or otherwise.

Further exemplary biopsy devices are disclosed in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pub. No. 2003/0109803, entitled "MRI Compatible Surgical Biopsy Device," published Jun. 12, 2003; U.S. Pub. No. 2007/0118048, entitled "Remote Thumbwheel for a Surgical Biopsy Device," published May 24, 2007; U.S. Provisional Patent Application Ser. No. 60/869,736, entitled "Biopsy System," filed Dec. 13, 2006; U.S. Provisional Patent Application Ser. No. 60/874,792, entitled "Biopsy Sample Storage," filed Dec. 13, 2006; and U.S. Non-Provisional patent application Ser. No. 11/942,785, entitled "Revolving Tissue Sample Holder for Biopsy Device," filed Nov. 21, 2007. The disclosure of each of the above-cited U.S. patents, U.S. patent application Publications, U.S. Provisional patent applications, and U.S. Non-Provisional patent application is incorporated by reference herein.

In some settings, it may be desirable to mark the location of a biopsy site for future reference. For instance, one or more markers may be deposited at a biopsy site before, during, or after a tissue sample is taken from the biopsy site. Exemplary marker deployment tools include the MAMMOMARK®, MICROMARK®, and CORMARK® brand devices from Ethicon Endo-Surgery, Inc. of Cincinnati, Ohio. Further exemplary devices and methods for marking a biopsy site are disclosed in U.S. Pub. No. 2005/0228311, entitled "Marker Device and Method of Deploying a Cavity Marker Using a Surgical Biopsy Device," published Oct. 13, 2005; U.S. Pat. No. 6,996,433, entitled "Imageable Biopsy Site Marker," issued Feb. 7, 2006; U.S. Pat. No. 6,993,375, entitled "Tissue Site Markers for In Vivo Imaging," issued Jan. 31, 2006; U.S. Pat. No. 7,047,063, entitled "Tissue Site Markers for In Vivo Imaging," issued May 16, 2006; U.S. Pat. No. 7,229,417, entitled "Methods for Marking a Biopsy Site," issued Jun. 12, 2007; U.S. Pat. No. 7,044,957, entitled "Devices for Defining and Marking Tissue," issued May 16, 2006; U.S. Pat. No. 6,228,055, entitled "Devices for Marking and Defining Particular Locations in Body Tissue," issued May 8, 2001; and U.S. Pat. No. 6,371,904, entitled "Subcutaneous Cavity Marking Device and Method," issued Apr. 16, 2002. The disclosure of each of the above-cited U.S. patents and U.S. patent Application Publications is incorporated by reference herein.

It may be desirable to deploy markers from a cannula type deployer into the biopsy site, such as a flexible tubular deployer. The marker should not unintentionally fall out of the deployer, and the force to deploy the marker should not be excessive.

SUMMARY

Above referenced U.S. patent application Ser. No. 12/196,301 illustrates a biopsy marker deployment device that can include marker engaging element. The marker engaging element can be employed to prevent a marker from prematurely exiting the deployer tube.

Applicant has determined that in some instances, it may be desirable to prevent premature marker deployment without the use of marker engaging element such as shown in Ser. No. 12/196,301, and without use of features that may increase the force required to deploy a marker from a marker delivery device.

For instance, Applicant has recognized the desirability of preventing premature marker deployment without substantially adding to the force needed to deploy a marker. Additionally, Applicant has recognized the desirability of providing a marker blocking member that blocks marker deployment, such as while the delivery device is within a package.

Still further, Applicant has recognized the desirability of providing a marker blocking member that may be removed from the delivery device without activating the push rod or other deployment apparatus used to direct the markers from the marker tube. Accordingly, activation of the push rod can be accomplished without excessive force, and without the need to expel or otherwise move a member positioned in the tube distal of the biopsy marker (or biopsy markers if a plurality of markers are included in the tube).

In one non-limiting aspect, the present invention provides a biopsy marker deployer comprising a tube, a marker exit, and at least one marker disposed in the tube. A marker blocking member is disposed in relation to the exit to prevent premature deployment of the marker (or markers) from the deployer. The blocking member may be releasably inserted within the exit of the cannula, such that the blocking member is removable from the cannula without advancing a push rod or other deployment actuator associated with the marker delivery device.

In one embodiment, the blocking member may include a proximal end and a distal end inclined with respect to the proximal end. The proximal end of the blocking member may be disposed substantially at or distal of the proximal end of the exit through which the marker(s) are deployed from the cannula. For instance, at least half the length of the blocking member, and more particularly substantially the full length of the blocking member may be disposed distal of the proximal end of the exit.

The distal face can be disposed adjacent a ramp disposed in the deployer, the ramp positioned with respect to the marker exit for facilitating marker deployment through a side (lateral) marker exit.

In one non-limiting aspect, the invention may also provide an assembly comprising: an outer package; an inner package component disposed within the outer package; and a biopsy marker delivery device disposed within the outer package. The biopsy marker delivery device may comprise an elongate hollow tube, a side (lateral) marker exit, and at least one marker disposed within the tube and deployable from the tube through the marker exit. The delivery device includes a marker blocking member disposed in the marker delivery device such that the blocking member prevents deployment of the at least one marker from the tube within the package.

The marker blocking member may be adapted to releasably engage the inner package component. Accordingly, the marker blocking member can act to prevent unintended marker deployment, and the marker blocking member can be removed from the marker delivery device without the need for actuating the delivery device. For instance, where the delivery device employs a push rod actuator or other marker pushing member, the marker blocking member is removed from the deployment tube when the marker is removed from the packaging, and without the need to advance or partially advance the push rod actuator.

BRIEF DESCRIPTION OF THE DRAWINGS

It is believed the present invention will be better understood from the following description of certain examples taken in conjunction with the accompanying drawings, in which like reference numerals identify the same elements and in which.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Figure 1:
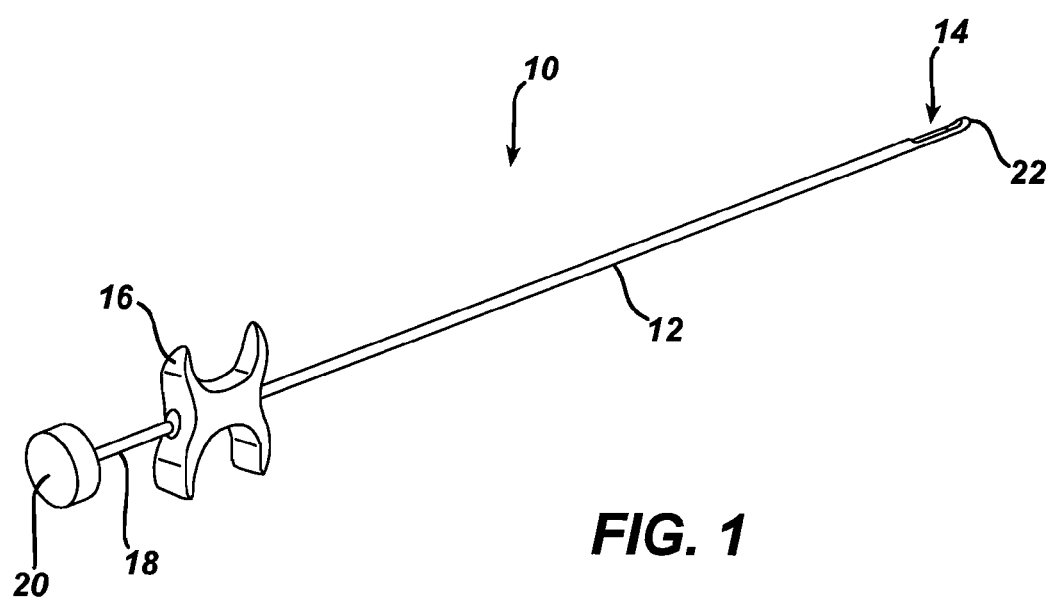
FIG. 1 depicts a perspective view of a marker delivery device of the type illustrated in U.S. patent application Ser. No. 12/196,301 filed Aug. 22, 2008.
Figure 2:
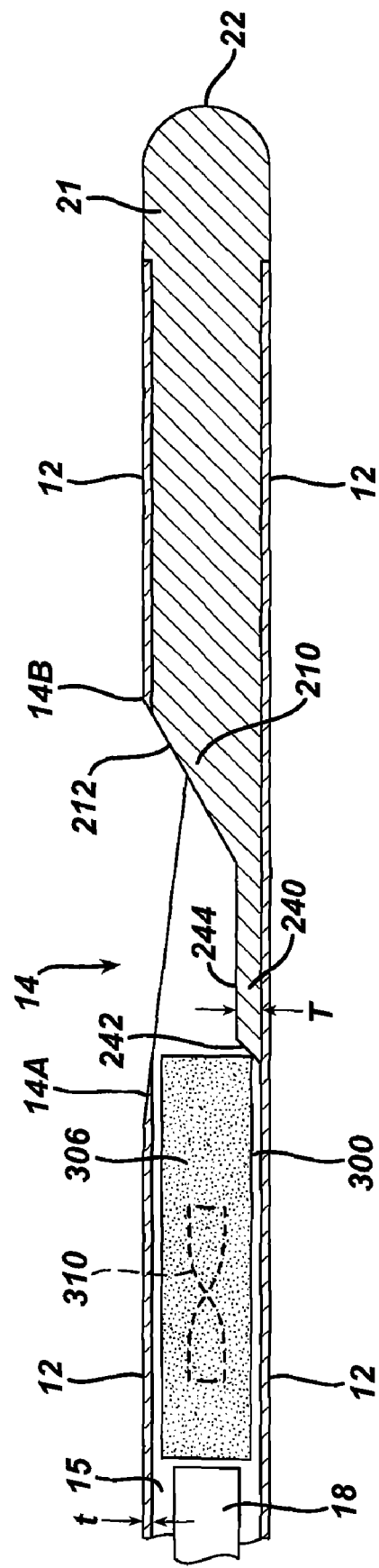
FIG. 2 depicts a cross-sectional view of a distal portion of a marker delivery device of the type illustrated in U.S. patent application Ser. No. 12/196,301 filed Aug. 22, 2008.
Figure 3:
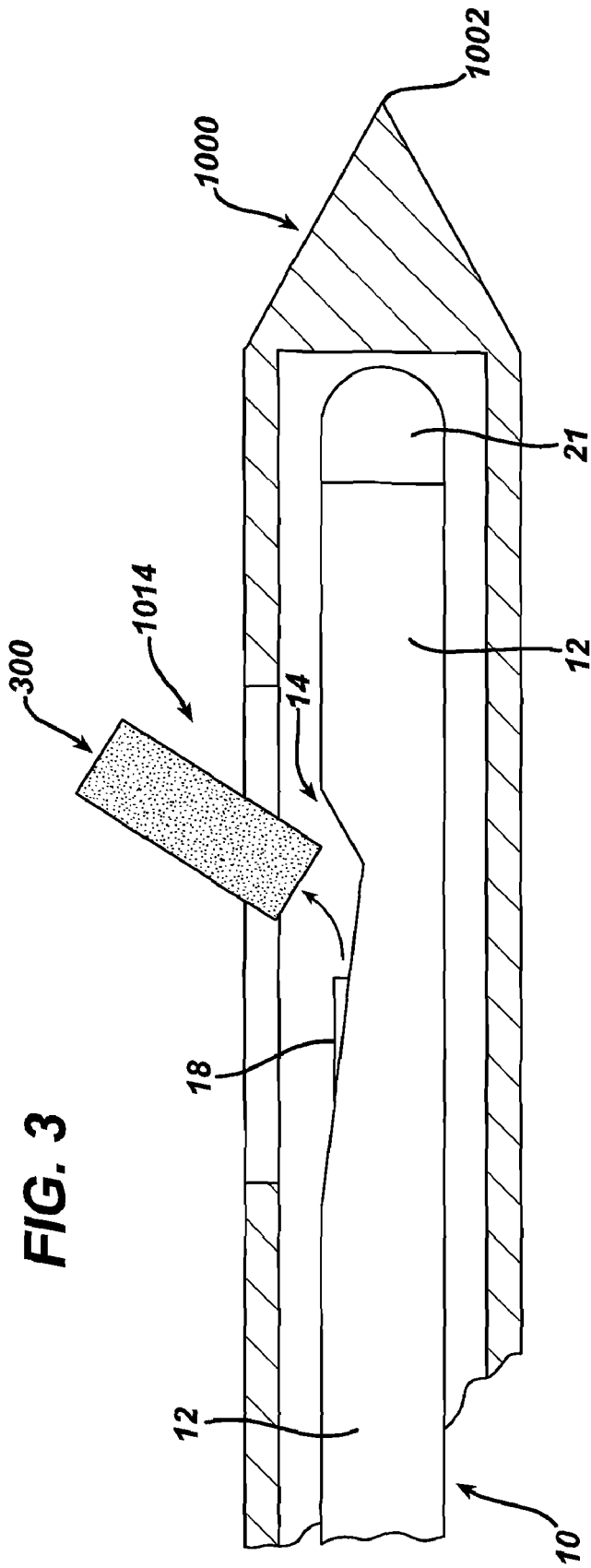
FIG. 3 depicts a marker being deployed from a deployer and through a lateral tissue receiving port in a biopsy needle to mark a biopsy site, such as illustrated in U.S. patent application Ser. No. 12/196,301 filed Aug. 22, 2008.
Figure 4:
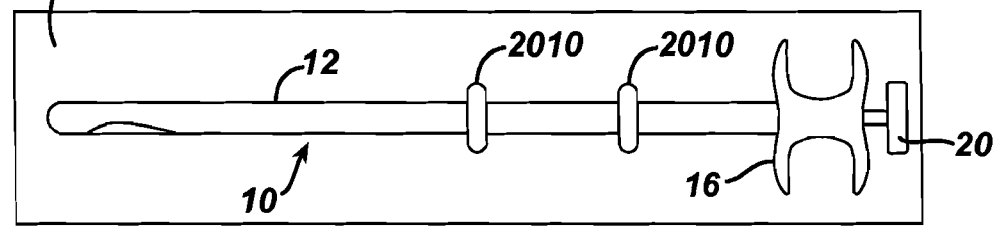
FIG. 4 depicts a prior art package component in the form of a cardboard mount supporting a biopsy marker deployer, where the tube of the deployer is held to the mount with one or more straps.

FIGS. 1-3 illustrate a marker delivery device 10 of the type illustrated in U.S. patent application Ser. No. 12/196,301 filed Aug. 22, 2008. The description below for FIGS. 1-3 is made for background purposes and with reference to the device shown in Ser. No. 12/196,301. FIG. 4 illustrates a depiction of a prior art arrangement for supporting biopsy marker delivery device on a packaging component. FIG. 5-9 illustrate one or more embodiments of a marker delivery device and assembly according to one or more embodiments of the present invention.

Referring to FIG. 1-3, marker delivery device 10 may include a tubular elongate outer cannula 12 having a marker exit, such as side opening 14 formed near to, but which can be spaced proximally from, the distal end of the cannula 12.

A grip 16 can be provided at the proximal end of cannula 12. An actuator, such as pushing member in the form of a push rod 18 can be provided, with push rod 18 extending coaxially in cannula 12 such that the push rod 18 is configured to translate within cannula 12 to displace one or more markers through the side opening 14 (see FIG. 2). Rod 18 can have a proximal portion having sufficient rigidity in compression to push a marker from the internal lumen of cannula 12 out through opening 14, and include a more distal portion that is relatively flexible in bending so that the cannula 12 can be inserted along a curved path to deploy a marker element at a biopsy site.

A plunger 20 can be provided at the proximal end of rod 18 for forcing rod 18 distally in cannula 12 to deploy a marker out of the cannula 12. A user may grasp grip 16 with two fingers, and may push on plunger 20 using the thumb on the same hand, so that the marker delivery device 10 can be operated by a user's single hand. A spring (not shown) or other feature may be provided about rod 18 to bias rod 18 proximally relative to grip 16 and cannula 12.

FIG. 2 depicts a cross-sectional view of a distal portion of the marker delivery device 10 of FIG. 1. FIG. 2 shows a biopsy marker 300 disposed in the internal lumen 15 of the cannula 12. The marker 300 can comprise a biodegradable or otherwise resorbable body 306, such as a generally cylindrically shaped body of collagen, and a metallic, generally radiopaque marker element 310 (shown in phantom) disposed within or otherwise carried by the body 306.

The cannula 12 can be formed of any suitable metallic or non-metallic material. In one embodiment, the cannula 12 is formed of a thin walled flexible hollow tube formed of a suitable medical grade plastic or polymer. One suitable material is a thermoplastic elastomer, such as Polyether block amide (PEBA), such as is known under the tradename PEBAX. The cannula 12 can be formed of PEBAX, and can be substantially transparent to visible light and X-ray.

The side opening 14 can be formed by cutting away a portion of the wall of cannula 12. The side opening 14 communicates with an internal lumen 15 of the cannula. The side opening 14 can extend axially (in a direction parallel to the axis of the lumen 15) from a proximal opening end 14A to a distal opening end 14B, as illustrated in FIG. 2.

The distal tip 22 extending from the distal end of cannula 12 can be rounded as shown in FIG. 2. Referring to FIG. 2, a marker delivery device can have the distal end of the cannula 12 closed by a unitary endpiece 21 formed in place in the distal end of the cannula 12, with a part of the endpiece 21 extending into the internal lumen 15 of the cannula. The distal endpiece 21 can be a molded or cast component, and can provide an integrally formed combination of the tip 22, a ramp 210 having a ramp surface 212, and a marker engaging element 240. The ramp surface 212 aids in directing the marker 300 from the internal lumen 15 through side opening 14.

The marker engaging element 240 (shown in FIG. 2 with thickness T) is described in the above Ser. No. 12/196,301. The element 240 is generally not required for use with the present invention. The present invention, as described below with reference to FIGS. 5-9, can be practiced without the need for the marker engaging element 240.

If desired, the tip 22 can be formed of, or include, a material that is relatively more radiopaque than the wall of the cannula 12. For instance, where the element 240, ramp 210, and tip 22 are formed as an integral endpiece 21, the endpiece 21 can include a radiopaque additive, such as barium sulfate. For instance, the endpiece 21 can be a component molded of PEBAX, with about 20 percent by weight barium sulfate added to the molten PEBAX mold composition.

Referring to FIG. 3, the marker delivery device 10 may be used to deploy a marker to mark a particular location within a patient. In FIG. 3, a cannular biopsy needle 1000 is shown. The needle 1000 is shown having a closed distal end with piercing tip 1002, and a lateral tissue receiving aperture 1014. Marker deployer 10 may be introduced to a biopsy site through biopsy needle 1000, which can be the same needle used to collect a tissue sample from the biopsy site. The biopsy needle 1000 can be of the type used with single insertion, multiple sample vacuum assisted biopsy devices. Several such biopsy devices are disclosed in the various patents and patent applications that have been referred to and incorporated by reference herein, though other biopsy devices may be used.

FIG. 3 shows the distal end of a marker deployer 10 disposed within the needle 1000. The needle 1000 can be positioned in tissue, and a biopsy sample can be obtained through opening 1014, thereby providing a biopsy cavity adjacent opening 1014. Then, after the tissue sample has been obtained and transferred proximally through the needle, and without removing the needle 1000 from the patient's tissue, the deployer 10 can be inserted into a proximal opening in the needle 1000. In FIG. 3, the needle 1000 and deployer 10 are positioned such that opening 14 of cannula 12 and opening 1014 of needle 1000 are substantially aligned axially and circumferentially. Then, with the deployer and needle so positioned at the biopsy site, the push rod 18 can be advanced to deploy the marker up the ramp surface 212, through the opening 14, and then through opening 1014, into the biopsy cavity.

FIG. 4 illustrates a known arrangement for supporting a biopsy marker delivery device 10 on a package component 2000. The package component 2000 can be a piece of cardboard or stiff paper based material disposed within sterile packaging. The biopsy marker delivery device 10 is shown fastened to the component 2000 by one or more straps 2010, which can be in the form of elastic filaments or wires which may be cut or otherwise undone to release device 10 from component 2000.

Figure 5:
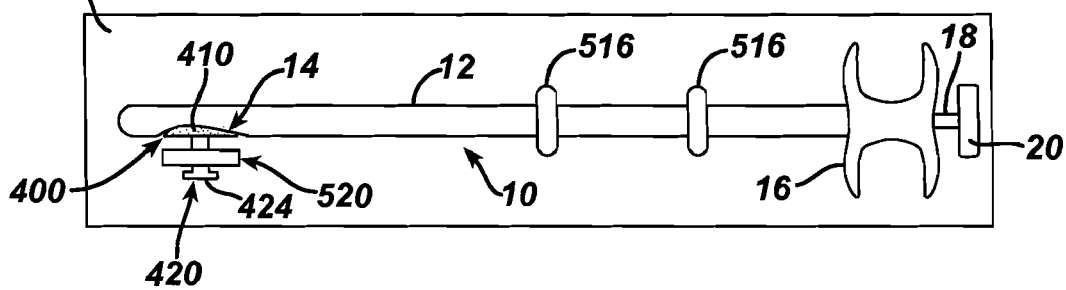
FIG. 5 depicts a marker deployment device and package component according to one embodiment of the present invention, illustrating the marker tube supported on a first portion of the package component and a marker blocking member including an anchor extending from the marker tube and engaging a second portion of the package component.

FIG. 5 illustrates a biopsy marker delivery device according to one embodiment of the present inventions. In FIG. 5, biopsy marker delivery device 10 is supported on a package component 500. The package component 500 may comprise cardboard or generally stiff paper stock. Package component 500 is shown including a generally planar portion 510 on which the device 10 is supported. FIG. 5 illustrates members, such as straps 516, for holding cannula 12 of the device on component 500, and generally stationary with respect to planar portion 510. The package component 500 is shown further including a second portion labeled 520. Second portion 520 may be a tab formed by selectively cutting and folding part of generally planar portion 510.

As shown in FIG. 5, the biopsy marker delivery device includes a biopsy marker blocking member 400 disposed at least partially within the marker exit provided by side opening 14. The blocking member 400 is shown disposed in the cannula 12, and is shown being at least partially visible in side opening 14. Side opening 14 provides the marker exit through which biopsy markers are deployed from cannula 12. Alternatively, a marker exit at the distal end of cannula 12 could be employed.

The marker blocking member 400 shown in FIG. 5 includes a first body portion, 410, and a second anchor portion 420. The body portion 410 is disposed at least partially within the exit of cannula 12. The second portion 420 extends generally radially outward from the cannula 12 to extend through tab portion 520 of the package component 500. The second portion 420 can include an enlarged end 424. The second portion 420 can extend through an opening in the tab portion 520, with the enlarged end 424 releasably engaging the tab portion 520 to maintain the body portion 410 of blocking member 400 in position with respect to the exit 14 and with respect to cannula 12 prior to use of the device 10.

Figure 6:
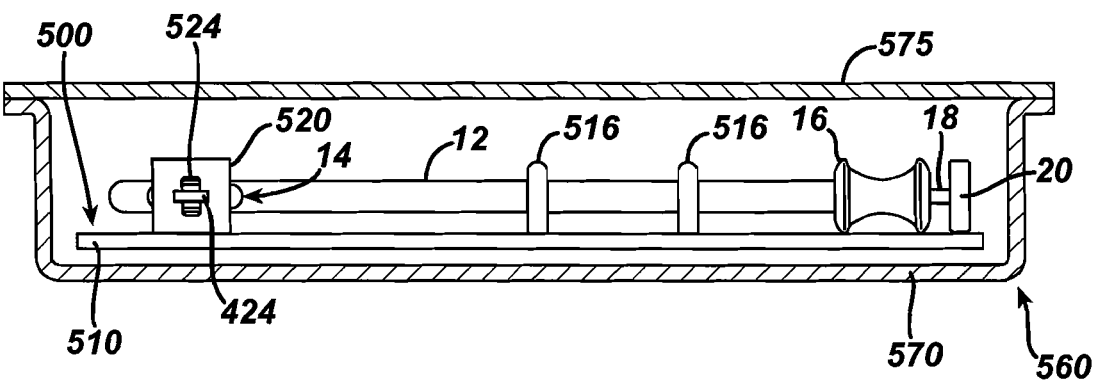
FIG. 6 illustrates an assembly according to one embodiment of the present invention, illustrating an outer package, an inner package component of the type shown in FIG. 5, the inner package component disposed within the outer package, the inner package component including a first generally planar portion supporting the marker delivery device, and the inner package component including a second portion, such an integral tab extending from the first portion, where the marker delivery device includes a marker blocking member having an anchor portion extending from the marker tube and through an opening in the tab to releasably engaging the tab.

FIG. 6 illustrates the internal package component 500 and device 10 disposed within an outer package 560. Outer package 560 can include an upper cover 575 releasably joined to a lower package portion 570. The package cover 575 can be releasably joined to the lower package portion 570 in any suitable manner, such as but not limited to by adhesive means, by ultrasonic welding, by heat sealing, and the like. For instance, the cover 575 and lower portion 570 may be made of similar, flexible packaging film stock. In FIG. 6, the lower portion 570 is illustrated in the form of a tray having an upper perimeter 573 to which cover 575 is releasably attached, and the lower portion 570 may also include sidewalls 574 and a bottom floor 572 on which the component 500 may be supported.

In FIG. 6, the tab portion 520 is shown extending generally vertically from and substantially perpendicular to the planar portion 510. An opening 524 cut (or otherwise formed) in tab portion 510 is sized to be slightly smaller in one dimension than a corresponding dimension of enlarged head 424. Accordingly, with cannula 12 held in place by members 516, and with the blocking member 400 held in place with respect to cannula 12 by the engagement of anchor portion 420 with tab 520, the blocking member 400 can be employed to prevent premature release of marker elements from the lumen of cannula 12.

Figure 7:
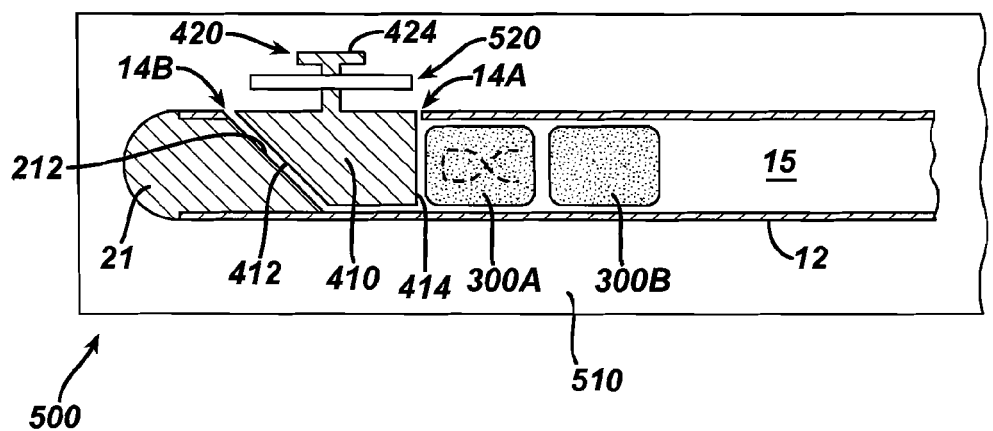
FIG. 7 is an enlarged illustration of the distal portion of a marker delivery and package component of FIG. 5, with the marker delivery device shown in partial cross-section and illustrating the marker blocking member having a body portion disposed within the tube lumen, the body portion having a proximal face disposed substantially at or distal of the proximal end of the lateral marker exit, an inclined distal face positioned adjacent a ramp associated with the marker exit, and the marker blocking member having an anchor portion extending from the body portion, the anchor portion extending through the tab of the package component and releasably engaging the tab.

FIG. 7 provides an enlarged illustration of the distal portion of a marker delivery device 10 and package component of FIG. 5, with the marker delivery device shown in partial cross-section and illustrating the marker blocking member 400 having a body portion 410 disposed within the exit 14 of tube lumen 15. In FIG. 7, two biopsy markers labeled 300A and 300B are shown positioned within cannula lumen 15 proximal of the blocking member 400.

The body portion 410 is illustrated having a proximal face 414 disposed substantially at or distal of the proximal end 14A of the marker exit 14. The body portion 410 is also shown having an inclined distal face 412 positioned adjacent to and facing the inclined surface of the ramp 212 associated with the marker exit. The body portion 410 may be sized and shaped to fit the space in lumen 15 bounded by (or otherwise defined by): the inclined ramp surface 212; the inner diameter of cannula 12; and an imaginary plane passing through the proximal end 14A of exit 14 and extending generally perpendicular to the axis of lumen 15. Accordingly, blocking member 400 may be removed from device 10 in a generally radially outward direction, without the need to advance the push rod, and without the need to translate the blocking member (or markers 300) in an axial direction.

Anchor portion 420 of blocking member 400 is shown extending in a generally radially outward direction from body 410, to extend from the marker exit 14 of cannula 12. The anchor portion 420 is shown including a neck 421 extending through the tab portion 520 of package component 500 (such as through opening 524 in the tab 520, the opening 524 illustrated in FIG. 8).

The end 424 of the anchor portion is enlarged relative to the neck 421, and the enlarged end 424 may be sized to have a length that is larger than one dimension (e.g. width) of the opening 524, and smaller than another dimension (e.g. length) of the opening 524, so that the enlarged end 424 may be inserted through opening 524 and is adapted to releasably engage the tab 520.

Figure 8:
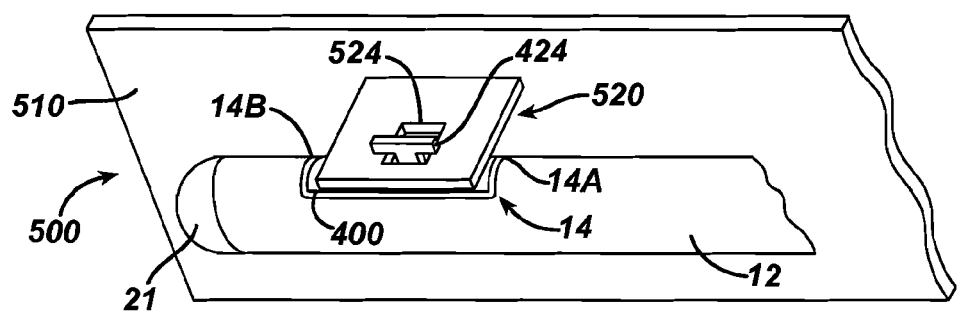
FIG. 8 is a perspective illustration of the distal portion of the marker delivery device including a blocking member.

FIG. 8 is a perspective illustration of the distal portion of the marker delivery device comprising marker blocking member 400. FIG. 8 illustrates the tab 520 with opening 524 through which anchor portion 520 extends.

In the figures, tab 520 is depicted as being generally perpendicular to planar component 510. However, if desired, tab 520 may bent or otherwise formed to at least partially overly the portion of the device 10 including the exit 14, and the tab may assist in holding the device 10 against the package component 500.

Figure 9:
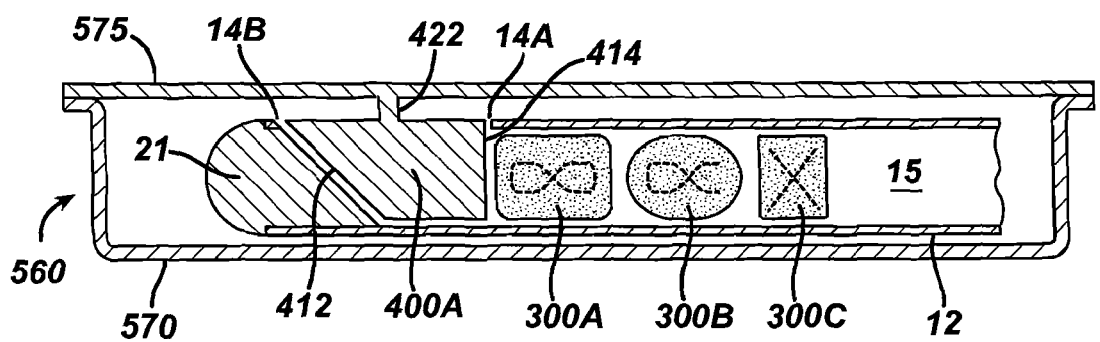
FIG. 9 is a cross-sectional illustration according to an alternative embodiment, showing a biopsy device disposed in outer packaging, and illustrating a marker blocking member having a portion disposed in the deployer tube and a portion of the member extending radially from the tube and joined to a top cover portion of the outer packaging.

FIG. 9 provides a cross-sectional illustration of an alternative embodiment, with biopsy device 10 shown disposed in outer packaging 560, and with the blocking member 400 connected to releasable top cover 575. Accordingly, removal of upper cover 575 from lower package portion 570 also serves to remove blocking member 400 from biopsy device 10.

In the embodiment shown in FIG. 9, the blocking member is shown having a connector portion 422 that is attached to upper cover 575. The blocking member 400 may be attached to cover 575 in any suitable manner, including but not limited to by use of adhesive attachment, heat welding, ultrasonic welding, and the like.

Embodiments of the devices disclosed herein are generally designed to be disposed of after a single use, but could be designed to be used multiple times. The packaging materials may be any suitable packaging materials, such as plastic or TYVEK bag.

The packaged biopsy device may then be placed in a field of radiation such as gamma radiation, x-rays, or high-energy electrons to sterilize the device and packaging. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. Accordingly, the scope of the present invention should be considered in terms of the following claims and is understood not to be limited to the details of structure and operation shown and described in the specification and drawings.

What is claimed:

1. A biopsy marker delivery device comprising:
 a hollow tube, a proximal end, a distal end, a marker exit having a proximal end and a distal end, and an internal lumen;
 a pushing member disposed at least partially within the internal lumen of the hollow tube;
 at least one biopsy marker disposed within the hollow tube distal of the pushing member and deployable from the marker exit by activating the pushing member;
 a marker blocking member engaged with the hollow tube, the blocking member sized and shaped to prevent the at least one biopsy marker from exiting the marker delivery device prematurely, wherein at least a portion of the member is disposed distally of the proximal end of the marker exit, wherein the marker blocking member is removable from the hollow tube prior to activating the pushing member; and
 a package component coupled with the marker blocking member and with the hollow tube, wherein the package component is operable to remove the marker blocking member from the internal lumen of the hollow tube upon removal of the hollow tube from the package component.

2. The device of claim 1 wherein the blocking member has a proximal end and a distal end, and wherein the proximal end of the member is disposed substantially at or distal of the proximal end of the marker exit.

3. The device of claim 1 wherein at least a portion of the blocking member extends outward of the lumen.

4. The device of claim 1 further comprising a ramp disposed in association with the marker exit for directing a marker through the exit, and wherein the blocking member has an inclined surface facing the ramp.

5. A biopsy marker delivery device comprising:
 a package component, comprising a locking feature;
 a hollow tube a proximal end, a distal end, a marker exit, and an internal lumen, wherein the hollow tube is engaged with the package component;
 a pushing member disposed at least partially within the internal lumen of the hollow tube;
 at least one biopsy marker disposed within the hollow tube distal of the pushing member and deployable from the marker exit; and
 a marker blocking member comprising a body portion and an anchor portion, wherein the body portion is engaged with the hollow tube, wherein the anchor portion is operatively associated with the package component, wherein the anchor portion is coupled with the locking feature of the package component such that the locking feature is operable to remove the body portion from the hollow tube upon disengagement of the hollow tube from the package component.

6. The device of claim 5 wherein the blocking member has a proximal end and a distal end, and wherein the proximal end of the member is disposed substantially at or distal of the proximal end of the marker exit.

7. The device of claim 5 wherein at least a portion of the member extends outward of the lumen.

8. The device of claim 5 further comprising a ramp disposed in association with the marker exit for directing a marker through the exit, and wherein the member has an inclined surface facing the ramp.

9. The device of claim 5 wherein the package component comprises a first portion supporting at least one of the hollow tube and the pushing member, and wherein the package component comprises a second portion, the blocking member being operatively associated with the second portion.

10. The device of claim 9 wherein the second portion comprises a flap integral with the first portion of the package component.

11. The device of claim 5 wherein blocking member comprises an anchor portion sized and shaped to engage the package component.

12. The device of claim 5 wherein the package component comprises a generally planar portion and at least one tab extending from the generally planar portion, and wherein the blocking member is adapted to releasably engage the at least one tab.

13. The device of claim 5 wherein at least one marker comprises collagen, and wherein the blocking member comprises a non-metallic.

14. An assembly comprising:
an outer package;
an inner package component disposed within the outer package;
a biopsy marker delivery device disposed within the outer package, at least a portion of the biopsy marker delivery device supported by the inner package component;
wherein the biopsy marker delivery device comprises an elongate hollow tube and at least one marker disposed within the tube and deployable from the tube through a marker exit; and
a marker blocking member coupled with the marker delivery device such that the blocking member prevents deployment of the at least one marker from the tube within the package, wherein the marker blocking member comprises an enlarged end, and wherein the enlarged end of the marker blocking member engages the inner package component, wherein the inner package component is operable to remove the marker blocking member from the marker delivery device when the inner package component is removed from the marker delivery device.

15. The assembly of claim 14 wherein the blocking member has a proximal end and a distal end, and wherein the proximal end of the member is disposed substantially at or distal of the proximal end of the marker exit.

16. The assembly of claim 15 wherein the blocking member comprises a first portion disposed in the tube, and a second portion extending out of at least a portion of the member extends outward of the lumen.

17. The assembly of claim 14 further comprising a ramp disposed in association with the marker exit for directing a marker through the exit, and wherein the blocking member has an inclined surface facing the ramp.

18. The assembly of claim 14 wherein the inner package component comprises a first portion supporting at least a portion of the biopsy marker delivery device, and a second portion, and wherein the marker blocking member is adapted to releasably engage the second portion.

19. The assembly of claim 14 wherein the second portion comprises a flap integral with the first portion of the inner package component, and wherein the marker blocking member comprising an anchor portion extending at least partially through the flap.

20. The assembly of claim 14 wherein the marker blocking member comprises a proximal face and a distal face, and wherein the distal face is inclined with respect to the proximal face.

* * * * *

UNITED STATES PATENT AND TRADEMARK OFFICE
CERTIFICATE OF CORRECTION

PATENT NO. : 8,371,443 B2  
APPLICATION NO. : 12/564315  
DATED : February 12, 2013  
INVENTOR(S) : Andrew P. Nock, Ramon Ramos and Shailendra K. Parihar Page 1 of 1

It is certified that error appears in the above-identified patent and that said Letters Patent is hereby corrected as shown below:

In the Claims:

Column 8, Claim 1, lines 26-27, reads "...a portion of the member is disposed..."; which should be deleted and replaced with "...a portion of the marker blocking member is disposed...."

Column 8, Claim 2, lines 38-39, reads "...the proximal end of the member is disposed..."; which should be deleted and replaced with "...the proximal end of the marker blocking member is disposed...."

Column 8, Claim 5, line 49, reads "...a hollow tube a proximal end..."; which should be deleted and replaced with "...a hollow tube having a proximal end...."

Column 9, Claim 6, line 1, reads "...the member is disposed..."; which should be deleted and replaced with "...the marking blocking member is disposed...."

Column 9, Claim 7, lines 3-4, reads "...a portion of the member extends..."; which should be deleted and replaced with "...a portion of the marking blocking member extends...."

Column 9, Claim 11, line 17, reads "...wherein blocking member...."; which should be deleted and replaced with "...wherein the marker blocking member...."

Column 10, Claim 14, line 4, reads "...within the package..."; which should be deleted and replaced with "...within the outer package...."

Column 10, Claim 16, line 18, reads "...extends outward of the lumen..."; which should be deleted and replaced with "...extends outward of a lumen...."

Column 10, Claim 19, line 28, reads "...of claim 14..."; which should be deleted and replaced with "...of claim 18...."

Signed and Sealed this  
Twenty-eighth Day of May, 2013

Teresa Stanek Rea  
*Acting Director of the United States Patent and Trademark Office*